(12) United States Patent  
Ohtsuka (10) Patent No.: US 7,682,566 B2  
(45) Date of Patent: Mar. 23, 2010

(54) SENSOR UNIT FOR ASSAY IN UTILIZING ATTENUATED TOTAL REFLECTION

(75) Inventor: Hisashi Ohtsuka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1071 days.

(21) Appl. No.: 11/333,207

(22) Filed: Jan. 18, 2006

(65) Prior Publication Data

US 2006/0159591 A1 Jul. 20, 2006

(30) Foreign Application Priority Data

Jan. 18, 2005 (JP) ............... 2005-010543

(51) Int. Cl.
| | |
|---|---|
| G01N 21/00 | (2006.01) |
| G01N 21/64 | (2006.01) |
| G01N 30/96 | (2006.01) |
| G01N 21/55 | (2006.01) |
| G01J 3/00 | (2006.01) |
| C12M 1/34 | (2006.01) |

(52) U.S. Cl. ............... 422/82.05; 422/82.07; 422/82.08; 422/82.09; 422/82.11; 422/88; 435/287.1; 356/73; 356/300

(58) Field of Classification Search ............... 422/82.07, 422/82.08, 82.11, 98, 99, 100, 102, 104, 422/88, 243; 435/283.1, 287.1; 356/73, 356/300; 436/150

See application file for complete search history.

(56) References Cited

U.S. PATENT DOCUMENTS

| | | | |
|---|---|---|---|
| 4,575,240 A | 3/1986 | Hess et al. | |
| 5,164,589 A | 11/1992 | Sjödin | |
| 5,313,264 A | 5/1994 | Ivarsson et al. | |
| 5,434,663 A * | 7/1995 | Maule | 356/300 |
| 2002/0127706 A1 | 9/2002 | Naya et al. | |
| 2003/0184755 A1 | 10/2003 | Mori et al. | |
| 2006/0153742 A1* | 7/2006 | Shimizu | 422/100 |

FOREIGN PATENT DOCUMENTS

| | | |
|---|---|---|
| JP | 6-3414 B2 | 1/1994 |
| JP | 3294605 B2 | 4/2002 |
| JP | 2002-296177 A | 10/2002 |
| JP | 2003-240705 A | 8/2003 |

OTHER PUBLICATIONS

JP 06-167443, Jun. 14, 1994, Tajima et al. (Machine Translated Version).*

* cited by examiner

*Primary Examiner*—Jill Warden  
*Assistant Examiner*—Dean Kwak  
(74) *Attorney, Agent, or Firm*—Sughrue Mion, PLLC (57) ABSTRACT

A surface plasmon resonance assay apparatus is loaded with a sensor unit. A sensing surface of a thin film detects reaction of a sample. A dielectric prism is overlaid with the thin film to constitute an interface. A reflection angle upon occurrence of attenuated total reflection of the illuminating light is changeable according to reaction of the sample on the sensing surface. Protecting panels are disposed to face outer surfaces of the prism, for covering and protecting at least partially the outer surfaces. A first window in one of the protecting panels is positioned on a path of the illuminating light traveling for incidence on the interface, for passing the illuminating light. A second window in one remaining protecting panel is positioned on a path of the illuminating light traveling upon reflection by the interface, for passing the illuminating light.

3 Claims, 6 Drawing Sheets

SENSOR UNIT FOR ASSAY IN UTILIZING ATTENUATED TOTAL REFLECTION

BACKGROUND OF THE INVENTION

1. Field of the Invention

The present invention relates to a sensor unit for assay in utilizing attenuated total reflection. More particularly, the present invention relates to a sensor unit for assay in utilizing attenuated total reflection, in which a prism as an optical element can be prevented from scratches, dirt or other damages.

2. Description of the Related Art

An assay apparatus assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. A thin film/dielectric interface of a metal film is fitted on a dielectric block. Light is directed to the thin film/dielectric interface in a manner conditioned for total reflection. Surface plasmon is a term to mean the compressional wave created on the surface of the metal and included in plasmon as quantized expression of the compressional wave. Free electrons in a metal vibrate to generate the compressional wave.

In the assay apparatus, the sensing surface is positioned opposite to the interface where the metal thin film is connected with the dielectric block. The sensing surface is caused to create surface plasmon resonance. Reaction of samples is assayed by detecting the SPR on the sensing surface.

Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A resonance angle or an angle of incidence of light for creation of surface plasmon resonance depends upon a refractive index of a medium of transmission of evanescent waves and surface plasmon. In other words, a change in the refractive index of the medium of transmission causes a change in the resonance angle of creation of SPR. The substance or sample in contact with the sensing surface is the medium for transmitting the evanescent waves and surface plasmon. When binding, dissociation or other reaction occurs on the sensing surface between two molecules or samples, the resonance angle changes because of a change in the refractive index of the medium of transmission. The SPR assay apparatus finds the changes in the resonance angle, to assay the interaction between the molecules or samples.

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like. A sample or biomaterial, such as protein, is handled as sample fluid for the purpose of preventing deactivation or modification due to drying. The sample fluid contains biomaterial and fluid medium, examples of which include pure water, physiological saline water, liquid buffer and the like.

JP-A 6-167443 disclose an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection. A sensing surface is overlaid inside the flow channel, for immobilizing the sample. Ligand fluid is introduced to the flow channel for immobilizing the ligand on the sensing surface. After this, analyte fluid is introduced for contact of the analyte and the ligand, to assay the interaction between those.

U.S. Pat. No. 5,164,589 and U.S. Pat. No. 5,313,264 (corresponding to JP-B 3294605) discloses a sensor of the chip type, which according to the SPR system is placed on the assay stage, the sensor including a glass base board which is dielectric and transparent, and metal film overlaid thereon. A plurality of sensors of the chip type are contained in a case. The case has a first opening for appearance of the sensing surface, and a second opening, positioned opposite to the first opening, for appearance of a back surface reverse to the sensing surface. The sensors are loaded in the assay apparatus removably in a state contained in the case. A prism is disposed on the assay apparatus. An upper surface and the glass substrate is connected by use of the matching oil. After the sensors of the chip type are loaded, the ligand is immobilized on the sensing surface, and then assayed for interaction with an analyte.

However, there is a problem in the above assay by use of the sensor of the chip type. As the sensing surface appears externally, the sensing surface is likely to dry if removed from the assay apparatus after the sample immobilizing flow. This is harmful to keeping characteristics of the ligand, for example, an enzyme characteristic of a protein as ligand is likely to deactivate. The assay must follow the sample immobilizing flow shortly for the purpose of preventing the drying of the sensing surface. The same assay stage is used for the immobilization and the assay process. The assay process would be impossible during the immobilization for next sample. The immobilization has a low speed of a rate-determining level defining the speed of the entire assay system even though the assay process is possible in a quick manner. Also, the necessity of the matching oil for the glass board and the prism causes high complexity of the placement of the sensor unit to the assay apparatus.

In U.S. Pat. Pub. No. 2002/0127706 (corresponding to JP-A 2002-296177) and U.S. Pat. Pub. No. 2003/0184755 (corresponding to JP-A 2003-240705), a sensor unit is disclosed in which a prism is used as a dielectric block, a sensing surface is constituted by an upper surface of the prism. A flow channel block is disposed higher than the sensing surface for flow of samples including a ligand and analyte. The sensor unit supports those elements fastened together. As the flow channel block is positioned at the sensing surface in the sensor unit, it is possible to preserve the sensing surface in a humid state after the sample immobilizing flow. Occurrence of failure due to the drying can be prevented. Also, high through-put can be obtained in operation because the sensor unit after the immobilization can be assayed serially one after another after collective immobilization of a plurality of the sensor unit.

In the sensor unit above having the prism, surfaces of the prism appears externally except for the sensing surface. There is a problem during handling of the sensor unit in occurrence of scratches or dirt outside the prism due to hands or fingers of a person conducting the assay. As the surfaces of the prism are used for entrance and exit of illuminating light, electric noise occurs due to absorption, attenuation or scattering of light caused by scratches or dirt. Precision in the assay is likely to be low. Specifically when the sensor unit includes the prism formed from plastic material, scratches are likely to occur because of the higher softness of the plastic material than glass. If dust sticks on the scratched surface, wiping of the prism may create additional scratches.

SUMMARY OF THE INVENTION

In view of the foregoing problems, an object of the present invention is to provide a sensor unit for assay in utilizing attenuated total reflection, in which a prism as an optical element can be prevented from scratches, dirt or other damages.

In order to achieve the above and other objects and advantages of this invention, a sensor unit is provided, having a thin film including a first surface and a sensing surface positioned reverse to the first surface for detecting reaction of a sample, and a transparent dielectric block, overlaid with the thin layer on the first surface to constitute an interface between, for causing incidence of illuminating light from a light source on the interface to satisfy a total reflection condition, and for causing the illuminating light reflected by the interface to travel and exit, wherein a reflection angle upon occurrence of attenuated total reflection of the illuminating light is changed according to reaction of the sample on the sensing surface. The sensor unit includes a protector, disposed to face an outer surface of the dielectric block, for covering and protecting at least partially the outer surface. Windows, formed in said protector, positioned on a path of said illuminating light traveling for incidence on said interface, and on a path of said illuminating light traveling upon reflection by said interface, for passing said illuminating light.

Preferably, the dielectric block is constituted by a prism, and the protector is positioned on two outer surfaces thereof.

Furthermore, a flow channel block has a flow channel, is secured to the dielectric block by orientation to set the flow channel at the sensing surface, the flow channel causing a flow of the sample fluid on the sensing surface. A sealing structure retains the flow channel block on the dielectric block, and closes the flow channel in a fluid-tight manner.

Preferably, the protector and the sealing structure are included in one piece.

Preferably, the flow channel has two orifices formed at respectively channel ends thereof, and is shaped to extend substantially in a U shape, and the orifices are open in one face of the flow channel block.

Preferably, the sealing structure squeezes the flow channel block and also engages with the dielectric block.

Preferably, the sealing structure includes a main panel secured to the flow channel block and positioned flush with the orifices. The protector includes first and second protecting panels, disposed on the main panel to extend erectly from a panel surface of the main panel.

Preferably, the first and second windows are window-shaped openings or window-shaped recesses formed in the first and second protecting panels.

Preferably, the sealing structure includes a retaining mechanism, formed on the first and second protecting panels, for engagement with the dielectric block. An access through hole is formed in the main panel, positioned at each of the orifices, for introduction or removal of the sample fluid.

According to one aspect of the invention, a sensor unit includes a protection layer, overlaid on an outer surface of the dielectric block, for protecting a region defined by passing the illuminating light of incidence on the interface, and a region defined by passing the illuminating light of reflection by the interface.

In one preferred embodiment, the protection layer is formed by applying a coating to the outer surface.

Preferably, the protection layer contains a metal oxide.

Preferably, the protection layer contains a fluoride.

In one preferred embodiment, the protection layer is constituted by a peelable protection tape, and the protection tape is peeled away before assay of the reaction of the sample.

According to the present invention, the sensor unit can have a prism as an optical element which can be prevented from scratches, dirt or other damages.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
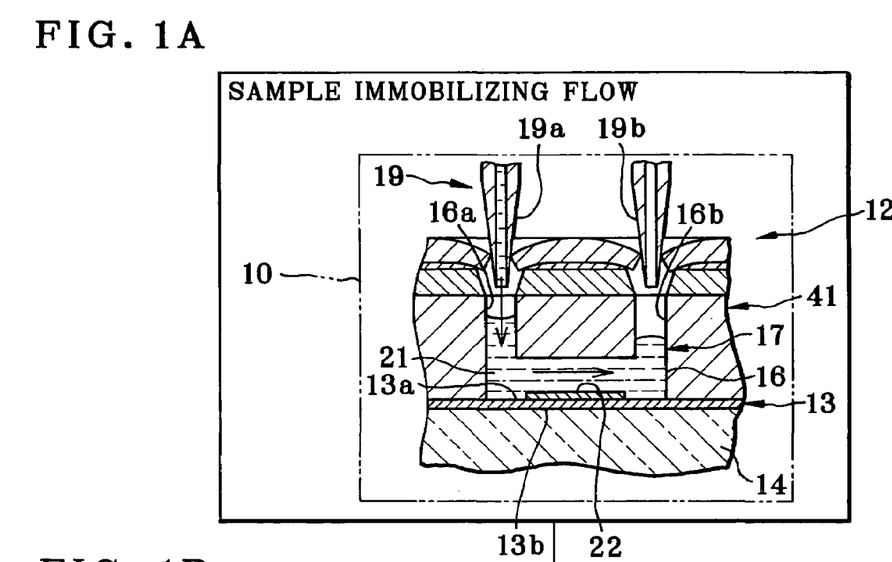
FIG. 1A is an explanatory view in section, illustrating a process of a sample immobilizing flow.
Figure 1B:
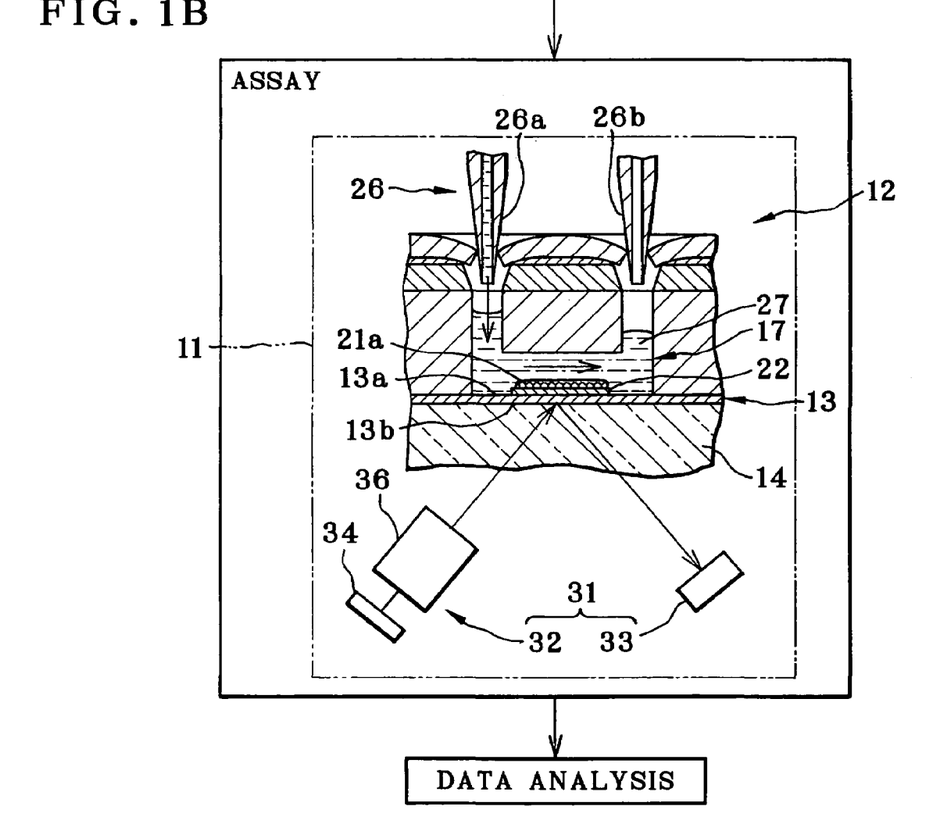
FIG. 1B is an explanatory view in section, illustrating processes of assay and data analysis.

In FIG. 1, a surface plasmon resonance (SPR) assay system is schematically illustrated. The assay system includes a sample immobilizing device 10, an assay apparatus 11 and a data analyzer. The sample immobilizing device 10 introduces fluid of ligand toward a sensing surface for the purpose of immobilizing the ligand. The assay apparatus 11 assays interaction between the ligand and an analyte introduced after the ligand immobilization. The data analyzer is provided with data from the assay apparatus 11, and analyzes the data.

Elements in a sensor unit 12 are referred to. The sensor unit 12 includes a prism 14, a thin film 13 of metal and a flow channel block or multi-channel flow cell 41. The prism 14 is overlaid with the thin film 13 on which biomaterial for assay is positioned. The flow channel block 41 includes a flow channel 16, which causes fluid of the biomaterial, namely ligand and analyte, to flow on to the thin film 13. An interface 13b is defined between the prism 14 and the thin film 13, and constitutes one thin film surface that is reverse to a sensing surface 13a of the thin film 13.

An example of material for the thin film 13 is gold (Au) or the like. A thickness of the thin film 13 is 50 nm. The thickness can be changed for the suitability in view of the material of the thin film 13, a wavelength of light to be applied, and the like. The prism 14 is a transparent dielectric block, and overlaid with the thin film 13. An illuminator 32 emits illuminating light, which is condensed by the prism 14 for application to the interface 13b to satisfy the total reflection condition. The flow channels 16 are in the U shape, and respectively include a flow recess, an entrance orifice 16a, and an exit orifice 16b. The entrance orifice 16a receives introduction of a sample fluid. The exit orifice 16b is accessed for draining the sample fluid. The flow channels 16 have an inner width or diameter of approximately 1 mm. An interval between the entrance and exit orifices 16a and 16b or the length of the flow recess is approximately 10 mm.

A lower side of the flow channels 16 where the flow recess is open is enclosed by the prism 14 having the sensing surface 13a. There are defined sensor cells 17 each of which is a portion of the sensing surface 13a closed by the portion about the recess. In the present embodiment, the sensor unit 12 has plural sensor cells 17, for example three.

A sample immobilizing flow is for binding of ligand on the sensing surface 13a of the linker film 22. At first, the sensor unit 12 is set in the sample immobilizing device 10. A pipetting type of fluid dispenser 19 is included in the sample immobilizing device 10, and has a dispensing pipette tip 19a and a removing pipette tip 19b. The dispensing pipette tip 19a is set at the entrance orifice 16a. The removing pipette tip 19b is set at the exit orifice 16b. The dispensing pipette tip 19a introduces fluid to the flow channel 16. The removing pipette tip 19b sucks and removes fluid from the flow channel 16. The introduction with the dispensing pipette tip 19a is at the same time as the removal with the removing pipette tip 19b. Ligand fluid 21 as sample fluid, as a fluid which contains ligand or biomaterial and fluid medium, is introduced through the entrance orifice 16a by the fluid dispenser 19.

A linker film 22 is overlaid on the thin film 13 and positioned at the flow channel 16 for immobilizing ligand. The linker film 22 is previously produced in the course of manufacturing the sensor unit 12. As the linker film 22 is a basis for immobilizing the ligand, various materials are available for selective use according to the type of the ligand to be immobilized.

In the sample immobilizing device 10, pre-treatment before a ligand immobilizing flow with the ligand fluid 21 is wetting of the linker film 22 by use of liquid buffer, and activation of the linker film 22 for the purpose of facilitating binding of the ligand to the linker film 22. An example of an immobilizing method is the amine coupling method. An example of material for the linker film is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). The sample immobilizing device 10, after the activation, introduces liquid buffer for the ligand immobilizing flow to wash and clean the flow channel 16.

Various liquids are available for use as the liquid buffer for the ligand immobilizing flow, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphate buffered saline (PBS) solution having strong operation of buffer and containing phosphate salt at high density which is not physiological, because protein can be electrified positively for the purpose of facilitating binding with the linker film 22.

The sample immobilizing device 10, after the activation and washing, introduces the ligand fluid 21 to the flow channel 16 for immobilization. Ligand 21a as sample such as biomaterial diffused in the ligand fluid 21, in introducing the ligand fluid 21, gradually comes near to and binds with the linker film 22. This is the ligand immobilizing flow of the ligand 21a on the sensing surface 13a. It is general that a step of the immobilization requires approximately one (1) hour, during which the sensor unit 12 is preserved in an environment conditioned suitably, for example at a conditioned temperature. Until the immobilization, the ligand fluid 21 in the flow channel 16 may be left to stand in a stationary state. However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the sensing surface 13a is completed, then the sample immobilizing device 10 removes the ligand fluid 21 from the flow channel 16. Namely, the removing pipette tip 19b discharges the ligand fluid 21 by suction. After this, the sensing surface 13a is washed by introducing washing liquid into the flow channel 16. In the sample immobilizing device 10, a blocking step is made after the washing. A blocking liquid is introduced into the flow channel 16, to deactivate the reaction group remaining without binding with the ligand. A preferable example of the blocking liquid is ethanol amine hydrochloride. After the blocking, the flow channel 16 is washed again. The sample immobilizing device 10 introduces evaporation retardant to the flow channel 16 after the final washing. The sensor unit 12 remains preserved until the assay with the sensing surface 13a humid on the evaporation retardant.

For the assay, the sensor unit 12 is set in the assay apparatus 11. A pipetting type of fluid dispenser 26 is installed in the assay apparatus 11, and structurally the same as the fluid dispenser 19 in the sample immobilizing device 10. The fluid dispenser 26 introduces fluid to the flow channel 16 through the entrance orifice 16a. For the assay in the assay apparatus 11, at first, liquid buffer is introduced into the flow channel 16, and caused to flow continuously for a prescribed time. After this, analyte solution or analyte fluid 27, as a fluid which contains analyte and fluid medium that may be solvent, is introduced into the flow channel 16. Then liquid buffer is introduced again. Note that the flow channel 16 may be cleaned or washed before initially introducing the liquid buffer. Reading of data in a photo detector starts upon initially introducing the liquid buffer in order to detect a reference level of a signal. The reading is continued until the introduction of the liquid buffer at the second time after entry of analyte fluid 27. It is possible not only to detect the reference level that is a base line, but to assay interaction or reaction between the analyte and the ligand, and to measure a signal until dissociation between the analyte and ligand in response to introduction of the liquid buffer.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand or analyte to determine suitably solution types and pH values of the solutions, and types of substances to be mixed, and their density. To facilitate dissolving of the analyte, dimethyl sulfo-oxide (DMSO) can be added to the physiological saline water. The use of the DMSO considerably influences to a level of an output signal. The buffer for assay is used for detecting the reference level of the signal, as described above. If DMSO is contained in the fluid for the analyte, it is preferable to use buffer for assay at a DMSO density approximately equal to that of the fluid in the analyte.

In general, the analyte fluid 27 may be kept preserved for a long time, for example one (1) year. It is likely that a difference occurs between an initial level and a current level of the DMSO density owing to a change with time. If assay with high precision is required, such a difference in the density is estimated according to the reference signal (ref-signal) level upon introducing the analyte fluid 27, so that measured data can be compensated for by DMSO density compensation. Compensation data for the DMSO density compensation is obtained before introducing the analyte fluid 27. A plurality of liquid buffers different in the DMSO density are introduced to the sensor cells 17. Amounts of changes in the levels of ref-signal and act-signal are evaluated so as to obtain the compensation data.

The optical assay unit 31 is constituted by the illuminator 32 and a photo detector 33. The reaction between the ligand and analyte can be recognized as a change of a resonance angle, which is an angle of incidence of light received by the interface 13b. To this end, the illuminator 32 is caused to apply light to the interface 13b at various values of angles of incidence satisfying a condition of the total reflection. The illuminator 32 includes a light source device 34 and an optical system 36, which includes a condensing lens, a diffusing plate and a polarizer. A position and angle of the installation of those elements are so determined that an angle of incidence of the light satisfies the condition of the above total reflection.

Examples of the light source device 34 include a light emitting diode (LED), laser diode (LD), super luminescent diode (SLD), and other light emitting element. A single element is used as the light source device 34 as a point light source, to illuminate the interface 13b in a sensor cell. Note that, if simultaneous assay of plural sensor cells is desired, light from a single light source device may be separated into plural light paths for application to the sensor cells. Alternatively, a plurality of light source devices may be arranged for association with respectively the sensor cells.

The diffusing plate diffuses light from the light source device 34, and suppresses onset of irregularity in the light amount. The polarizer allows only p-polarized light to pass, the p-polarized light creating the surface plasmon resonance. Note that no polarizer is required if directions of rays emitted by the light source device 34, for example an LD, are kept equal. However, a diffusing plate may be combined with the light source device 34 of a type of which directions of emitted rays are kept equal. Directions of rays in polarization are changed to an unequal state by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the interface 13b without irregularity in the intensity.

The photo detector 33 receives light reflected by the interface 13b of the thin film 13, and detects intensity of the light. Rays of light are incident upon the interface 13b at various angles. The light is reflected by the interface 13b at various angles of reflection according to the angles of the incidence. The photo detector 33 receives the light at various angles of the reflection. When a change occurs in the transmitting medium on the sensing surface 13a for surface plasmon, a refractive index changes to change a reflection angle in attenuation of light. When the analyte fluid is introduced to the sensing surface 13a, a resonance angle changes according to interaction between the analyte and the ligand. A reflection angle of attenuation of the light also changes.

An example of the photo detector 33 is a CCD area sensor or an array of photo diodes, which receives light reflected by the interface 13b at various angles of reflection, and photoelectrically converts the light into an output of SPR. The interaction between the ligand and analyte is recognized as information of shifting of a position of attenuation of the reflected light on the photo reception surface of the photo detector 33. A refractive index of the thin film with the sensing surface 13a of the linker film becomes different between the states before and after the contact of the ligand with the analyte. Thus the resonance angle at which surface plasmon resonance occurs changes between those states. When reaction starts by the contact between the analyte and ligand, the resonance angle starts changes, to start shifting the attenuation position of the reflected light on the photo reception surface. The photo detector 33 outputs and sends an SPR signal to the data analyzer. The data analyzer analyzes the SPR output from the assay apparatus 11, to recognize interaction between the analyte and ligand.

Figure 4:
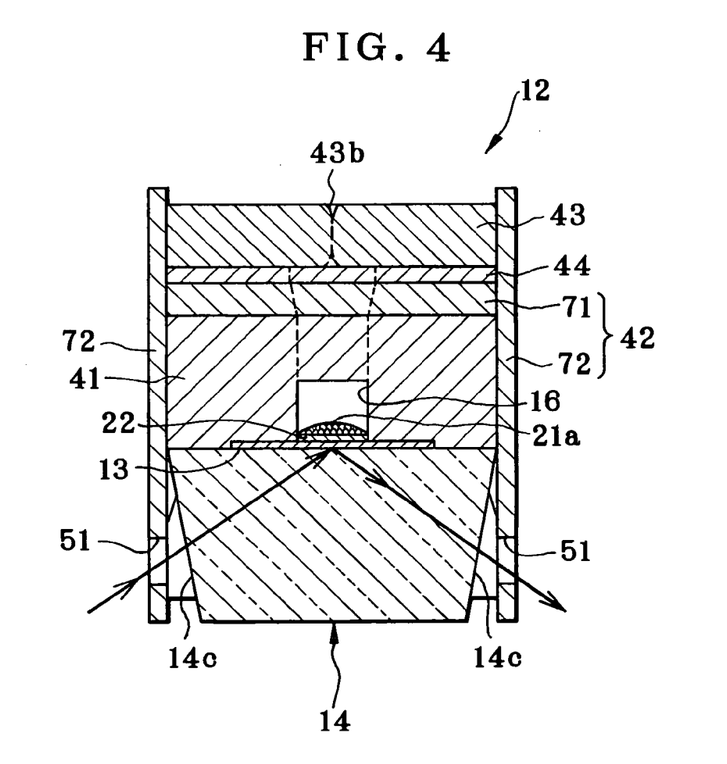
FIG. 4 is a cross section illustrating the sensor unit.

Note that in FIG. 4, the illuminator 32 and the photo detector 33 in the optical assay unit 31 are positioned so that a direction of light projected and reflected between those intersects horizontally with a flow of the flow channel 16, which is unlike the structure depicted in FIG. 1B. The state of FIG. 1B is simplified for the convenience. However, in the invention the illuminator 32 and the photo detector 33 may be positioned according to in FIG. 1B so that a direction of light projected and reflected between those is horizontally aligned with the flow of the flow channel 16 between the pipettes.

Figure 2:
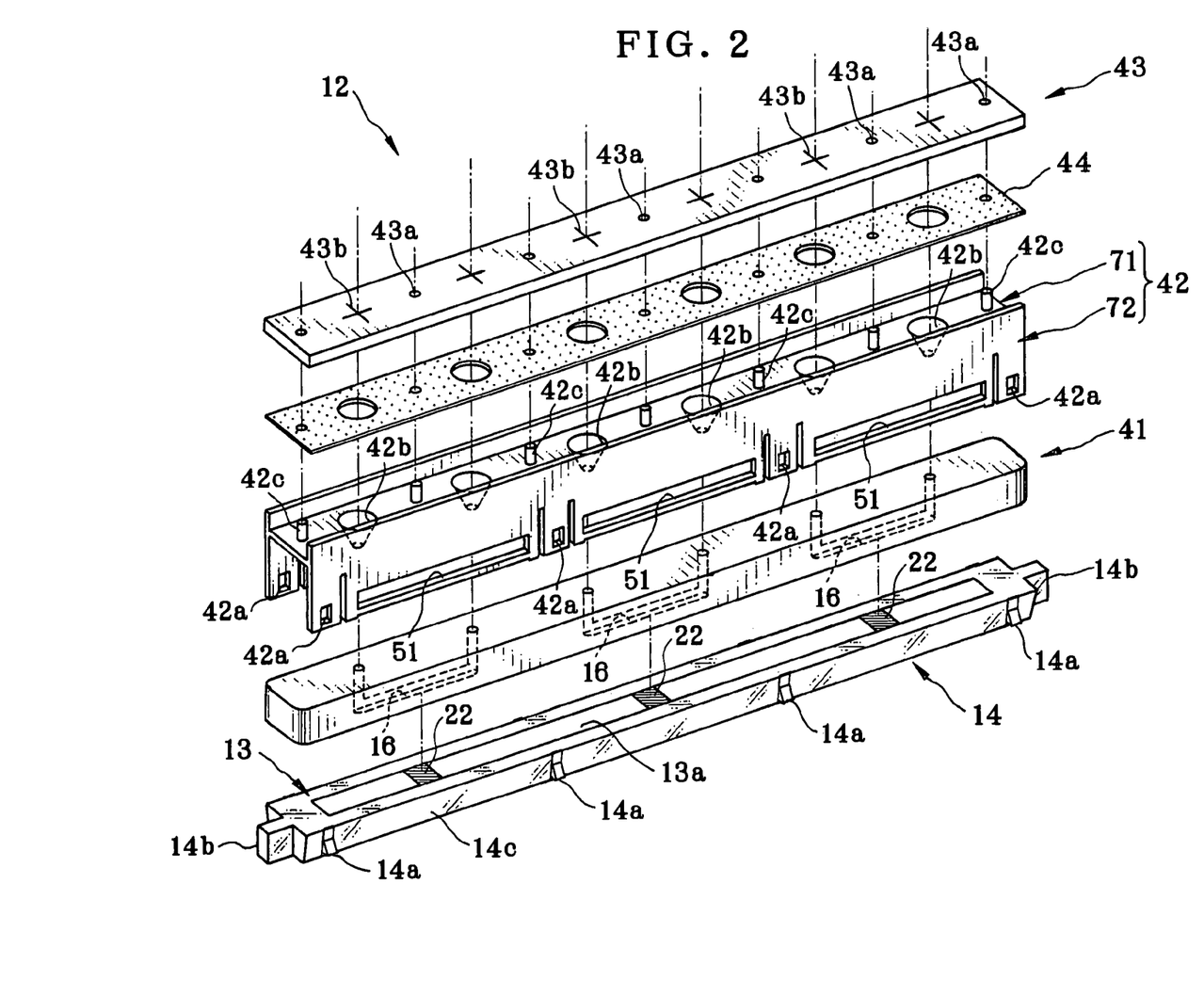
FIG. 2 is an exploded perspective view illustrating a sensor unit.

In FIG. 2, the sensor unit 12 is illustrated structurally. The sensor unit 12 includes the flow channel block 41, the prism 14, a sealing structure or sealing block 42, and a lid 43. The flow channel block 41 has the at least one flow channel 16 formed through the same. The prism 14 is dielectric, and is overlaid with the thin film 13 on its upper surface. The sealing structure 42 supports the flow channel block 41 by fitting its lower surface on the upper surface of the prism 14. The lid 43 is disposed higher than the sealing structure 42.

The flow channel 16, for example three (3) channels, are formed in the flow channel block 41. The flow channel block 41 has a long shape, in which the flow channels 16 are arranged in a direction of a block length. The flow channels 16 constitute the sensor cells 17 together with the thin film 13 in connection with its lower surface. See FIG. 1. The flow channel block 41 is formed from elastic material for the purpose of ensuring tightness in contact with the thin film 13. Examples of elastic materials include rubber, polydimethylsiloxane (PDMS), and the like. When a lower surface of the flow channel block 41 is pressed on an upper surface of the prism 14, the flow channel block 41 is elastically deformed, to remove a space between its surface and the thin film 13. Open lower portions of the flow channels 16 are closed fluid-tightly by the upper surface of the prism 14. Note that the number of the flow channels 16 may not be three, but can be one or two, or four or more.

Note that any suitable material and form can be used to construct the flow channel block 41 with the sealing structure 42, by utilizing various techniques in the field of the gasket for sealing.

The prism 14 has a length greater than a length of the flow channel block 41, and has an upper surface positioned on the three flow channels 16. The thin film 13 is formed by vapor deposition on the prism 14. The thin film 13 of a strip shape is positioned on a train of the flow channels 16. Also, the linker film 22 is formed on the upper surface of the thin film 13 for the flow channels 16.

An outer lateral surface 14c extends on the prism 14 on its lateral side. Light from the illuminator 32 enters through the outer surface 14c, and strikes the interface 13b reverse to the sensing surface 13a. The interface 13b reflects the illuminating light, which exits through a second one of the outer surfaces 14c. The photo detector 33 receives the exiting reflected light. As the outer surfaces 14c are surfaces for passage of the light, electric noise is likely to occur if scratches or dust occurs on the outer surfaces 14c.

Retaining claws 14a are formed to project from the prism 14 at its sides as viewed longitudinally. Fastening portions of the sealing structure 42 are engageable with the retaining claws 14a. The flow channel block 41 as a multi-channel flow cell is sandwiched between the sealing structure 42 and the prism 14. A lower surface of the flow channel block 41 is kept fitted on the prism 14. A unit including the flow channel block 41, the thin film 13 and the prism 14 is obtained.

Retaining projections 14b protrude from ends of the prism 14 as viewed in its longitudinal direction. A sensor holder (not shown) contains a plurality of sensor units 12 in the course of the sample immobilizing flow. The retaining projections 14b are formed for positioning the sensor unit 12 in a contained state by engagement with the sensor holder.

The sealing structure 42 includes an upper panel 71 or first panel and protecting lateral panels 72. The upper panel 71 covers an upper face of the flow channel block 41. The protecting panels 72 extend in the longitudinal direction of the upper panel 71. The sealing structure 42 is one molded piece having those portions. The upper panel 71 and the protecting panels 72 are disposed to intersect in an H shape as viewed in a section. The protecting panels 72 project to extend in a downward direction to cover the outer lateral surfaces 14c of the prism 14 in a skirt form.

An access through hole 42b is formed in the upper panel 71, and positioned at each of the entrance and exit orifices 16a and 16b of the flow channel 16, for entry of an end of each of dispensing and removing pipettes and the like. A lower face of the access through hole 42b is connectable with the entrance and exit orifices 16a and 16b of the flow channel 16 for flow of fluid. The access through hole 42b has a funnel shape with a decreasing diameter for introducing liquid ejected by the pipette toward the entrance orifice 16a. Rod shaped bosses 42c are formed to project beside the access through hole 42b. Holes 43a are formed in the lid 43. The bosses 42c are fitted in the holes 43a, to position the lid 43 firmly. Double sided adhesive tape 44 attaches the lid 43 to an upper surface of the sealing structure 42. Note that suitable holes are formed in the double sided adhesive tape 44, and associated with the access through hole 42b and the bosses 42c.

The lid 43 covers the access through hole 42b communicating to the flow channel 16, and prevents evaporation of liquid in the flow channel 16. The lid 43 is formed from rubber, elastomer, resin or other elastic material. A cross shaped access slit 43b is formed in the lid 43 and positioned respectively at the access through hole 42b. The lid 43 is required to cover the access through hole 42b in order to prevent liquid in the flow channel 16 from evaporation. However, no pipette can enter the access through hole 42b if covering of the lid 43 is complete.

So the cross shaped access slit 43b is formed to enable insertion of pipettes, and to close the access through hole 42b while no pipette is inserted. If a pipette is forcibly pressed into the cross shaped access slit 43b, its edges are elastically deformed, to allow receipt of the pipette by becoming open. See FIGS. 1A and 1B. When the pipette is externally pulled out, the cross shaped access slit 43b elastically closes the access through hole 42b again by returning to its initial state. Even while a pipette stands inserted in the cross shaped access slit 43b, edge portions of the cross shaped access slit 43b exert force of recovery to close the cross shaped access slit 43b. The access through hole 42b is kept closed as a space protected from external gas. Thus, fluid in the flow channel 16 is prevented from evaporation.

Figure 3:
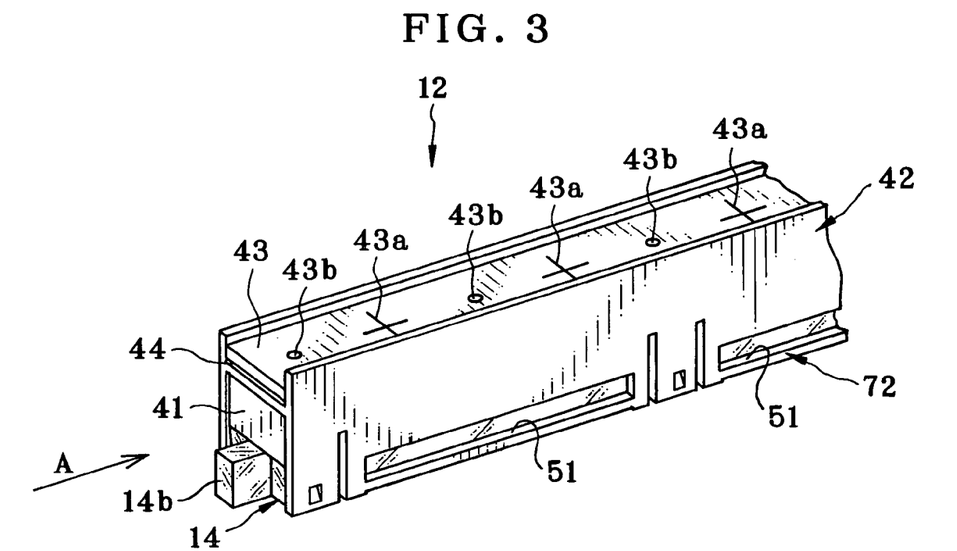
FIG. 3 is a perspective view, partially broken, illustrating the sensor unit.

In FIG. 3, the sealing structure 42 is placed on the flow channel block 41 to lie on its upside. An engaging hole 72a in the protecting lateral panels 72 is engaged with the retaining claws 14a of the prism 14. Thus, the flow channel block or multi-channel flow cell 41 is connected with the prism 14. The upper panel 71 is then attached with the flow channel block 41 by the double sided adhesive tape 44, to position the access through hole 42b at each of the entrance and exit orifices 16a and 16b. A lower end of the access through hole 42b is connected with any one of the entrance and exit orifices 16a and 16b, to connect the access through hole 42b with the flow channel 16. Fluid dispensed by the pipette tip is poured to flow into the entrance orifice 16a.

The protecting panels 72 are caused by the engagement of the sealing structure 42 with the prism 14 to extend along the outer lateral surfaces 14c of the prism 14 to cover the outer surfaces 14c. Thus, the outer surfaces 14c for entrance and exit of light are prevented from scratches or dirt as fingers or the like are prevented from touching the outer surfaces 14c even while the sensor unit 12 is handled. Windows 51 are formed in the protecting panels 72 in a number associated with the number of the sensor cells 17.

FIG. 4 is a section taken on a line in FIG. 3, and viewed in the direction A. Some of the windows 51 are disposed on a first light path where illuminating light travels from the illuminator 32 through one of the outer lateral surfaces 14c and to the interface 13b. Remaining ones of the windows 51 are disposed on a second light path where illuminating light travels from the interface 13b through a second one of the outer surfaces 14c and to the photo detector 33. The position and the size of the windows 51 are determined for ensuring the sufficient space of the first light path and second light path.

As the windows 51 are open, a finger or the like is likely to contact the protecting panels 72 through the windows 51. However, the windows 51 have a very small size so that no danger of contact of a finger remains. Note that the windows 51 can be an opening and a transparent panel or the like fitted therein. This is effective in reliably preventing the contact of a finger of the protecting panels 72.

As the protecting panels 72 having the windows 51 cover the outer lateral surfaces 14c of the prism 14, the light path from the illuminator 32 to the interface 13b and the light path from the interface 13b to the photo detector 33 can be ensured without blocked. The outer surfaces 14c can be protected from scratches, dirt or any damages.

Figure 5:
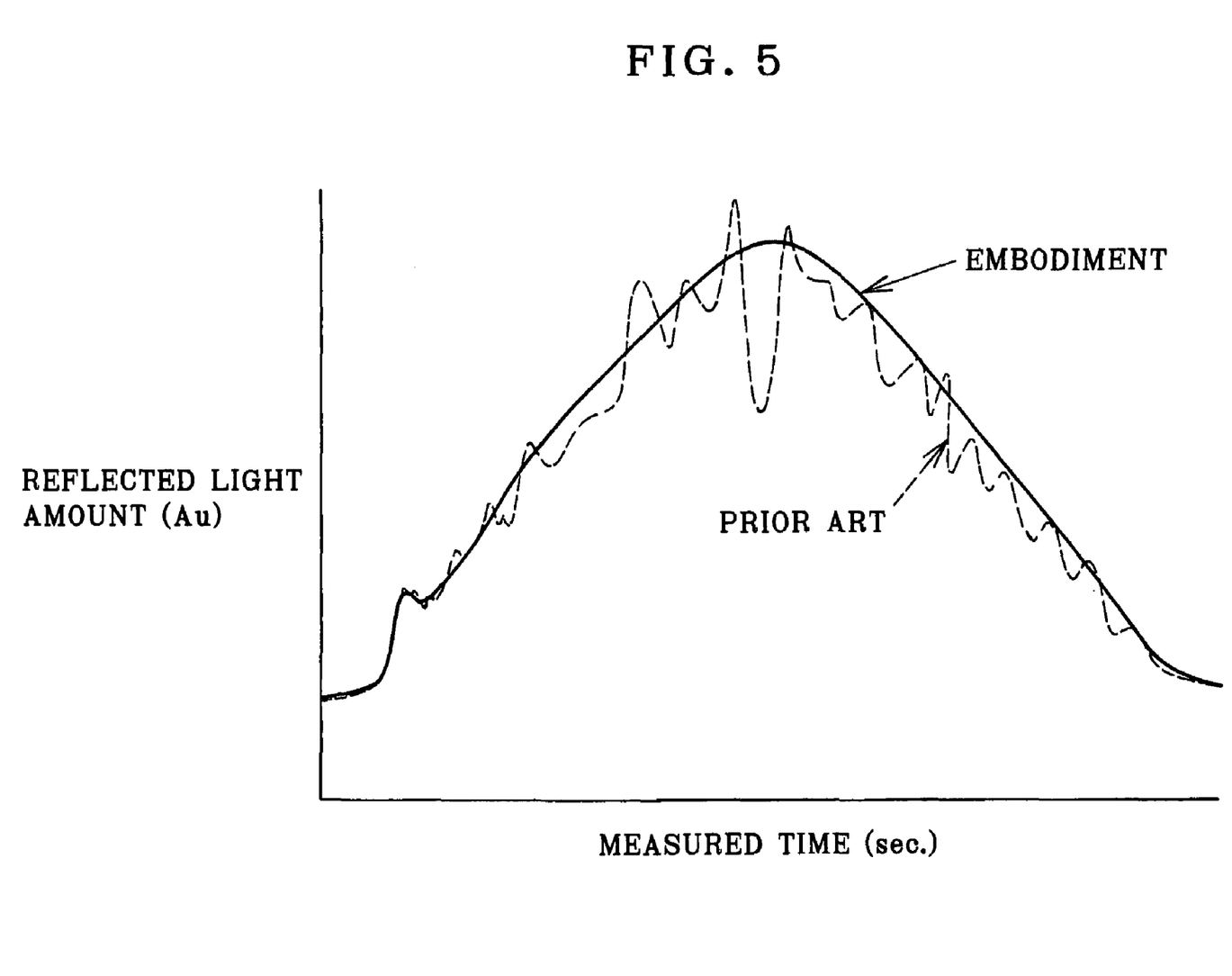
FIG. 5 is a graph illustrating an amount of reflected light as a result free from electrical noise.

FIG. 5 is a graph illustrating a comparison between light amounts of reflection in the SPR assay according to the prior art and the invention. It is found by the observation that electric noise due to scratches, dirt and the like can be suppressed during any portion of the period of the assay.

The operation of the above construction is described. For the process of the sample immobilizing flow, the sensor unit 12 is set in the sample immobilizing device 10. The sample is introduced for immobilization. When the immobilization is completed, the sensor unit 12 is set in the assay apparatus 11 for assay. As the outer lateral surfaces 14c of the prism 14 are covered by the protecting panels 72 in the sensor unit 12, the prism 14 is protected from occurrence of scratches, dirt of the like while handled. Also, portions of the outer surfaces 14c outside the windows 51 are covered by the protecting panels 72. Sticking of dust, dirt or the like floating in the atmosphere can be suppressed.

In the above embodiment, the windows 51 are in a quadrilateral shape. However, the windows 51 may be in any suitable shape, for example elliptical shape, for defining light paths of entrance and exit.

It is noted that the sealing structure 42 may be constituted by two or more pieces in combination including the upper panel 71 or first panel and the protecting panels 72. An advantage of the sealing structure 42 as one piece, however, can be obtained because of the smaller number of parts and a lower cost of the manufacture.

Figure 6:
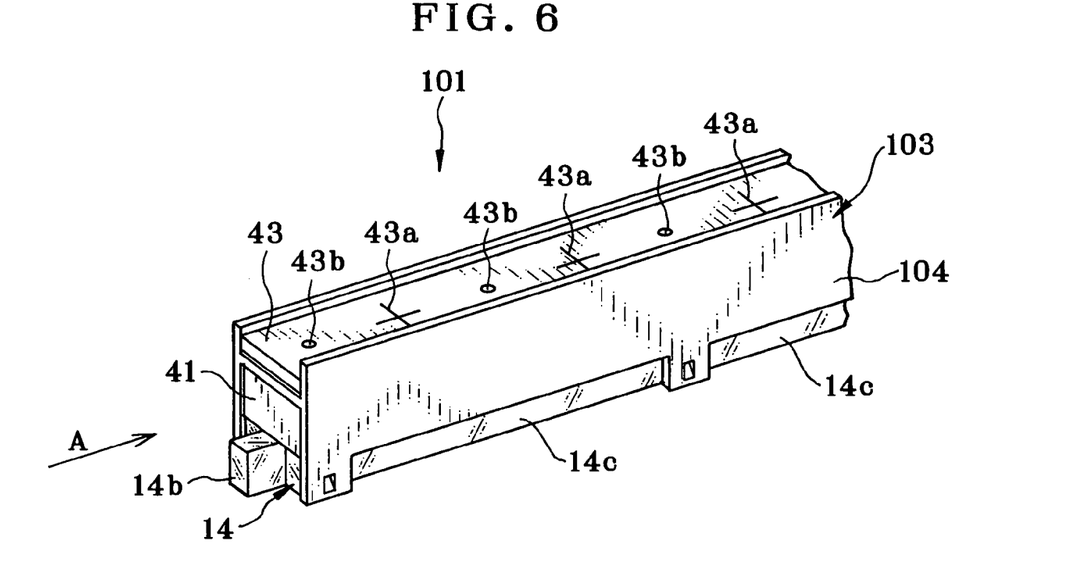
FIG. 6 is a perspective view, partially broken, illustrating the sensor unit.
Figure 7:
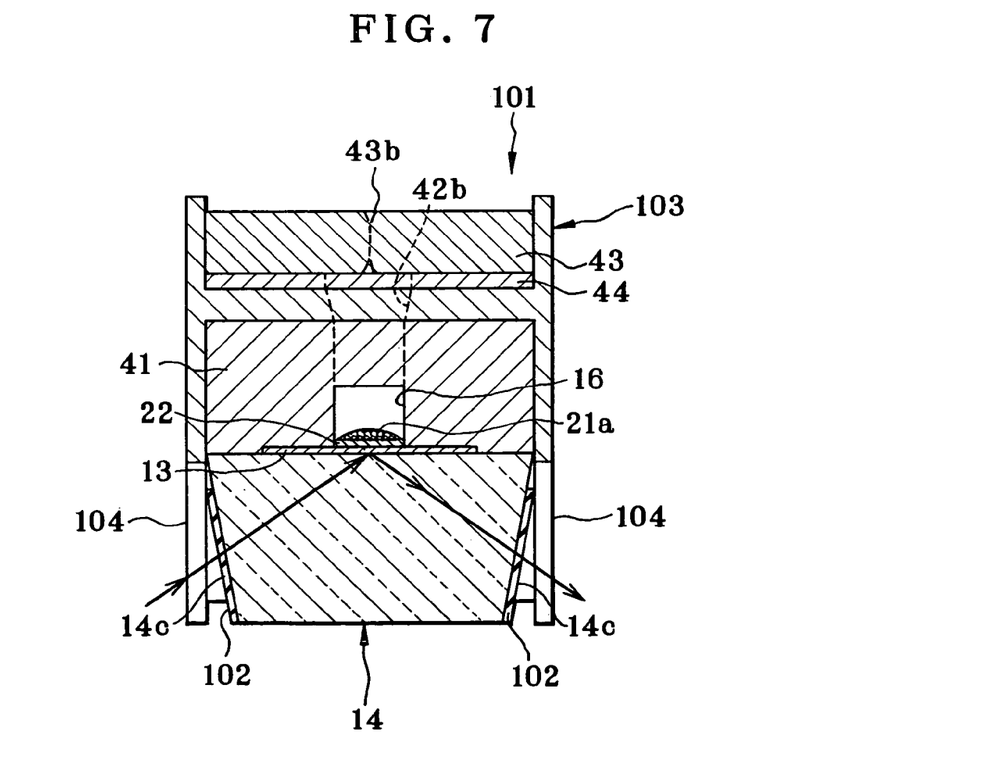
FIG. 7 is a cross section illustrating the sensor unit.

In FIGS. 6 and 7, another preferred embodiment of the invention is illustrated. Elements similar to those in the above embodiment are designated with identical reference numerals. A sensor unit 101 includes a sealing structure or sealing block 103, of which lateral panels 104 have such a height that at least portions of the outer lateral surfaces 14c appear without covering even with the sealing block 103 placed on the prism 14. The lateral panels 104 have a height short of a size sufficient for covering the outer surfaces 14c. A protection layer 102 in a transparent form is overlaid on each of the outer surfaces 14c in the sensor unit 101, which is instead of the windows 51 in the protecting panels 72.

The protection layer 102 is a surface protection layer, film, sheet or coating on the outer lateral surface 14c obtained in a transparent form. An example of material of the surface protection layer is an inorganic hard coat composition containing magnesium fluoride and titanium oxide. However, any suitable transparent compositions or substances may be used for the purpose of preventing scratches, dirt and the like. Also, the hard coat material operates also as a non-reflection coat. This is effective in increasing an amount of transmitted light in comparison with the lack of the coating, and in suppressing influence of interference of light due to multiple reflection.

Figure 8A:
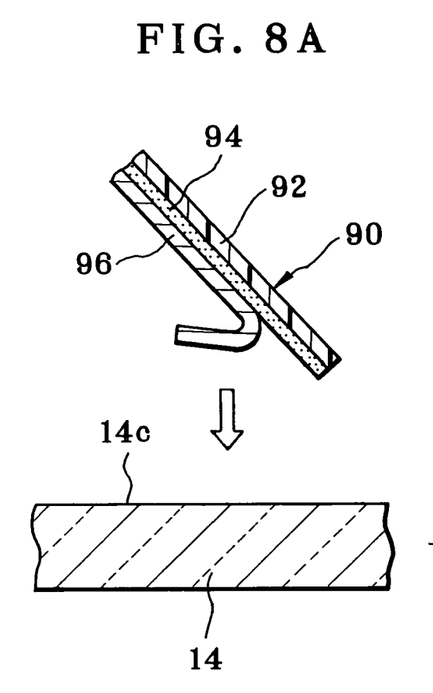
FIGS. 8A and 8B are explanatory views in section, illustrating use of an adhesive protecting tape.
Figure 8B:
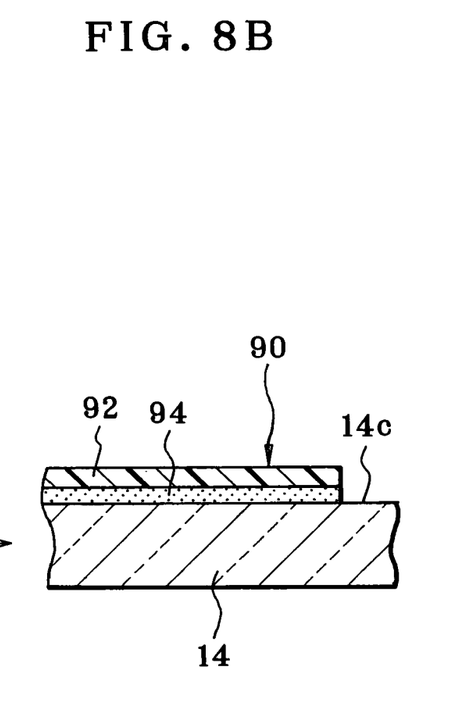

Another preferred embodiment is described, in which a protection tape 90 of FIGS. 8A and 8B is fitted on the outer lateral surfaces 14c instead of the coating. The tape 90 includes a support 92 of polymer film and a pressure-sensitive adhesive agent 94 overlaid thereon, and is secured to the outer surfaces 14c of the prism 14 in a peelable manner. As the pressure-sensitive adhesive agent 94 is included, no high transmittance can be obtained for the purpose of assay no matter whether the support 92 of polymer film is transparent. Consequently, the support 92 of polymer film of the protection tape 90 is peeled from the outer surfaces 14c of the prism 14 before the start of the assay. Specific examples of protection tapes include Plus Cover (trade name) in a three-layer form of a soft transparent non-oriented polypropylene film, acrylic pressure-sensitive adhesive agent 94, and release paper 96, and include Pachicut (trade name, manufactured by Dainippon Ink and Chemicals, Incorporated) in a four-layer form of a soft transparent non-oriented polypropylene film, electrically conductive resin, acrylic pressure-sensitive adhesive agent 94, and release paper 96. Among those, Pachicut is preferable in particular because of relatively high antistatic performance, which suppresses electrostatic sticking of dust at the time of peeling.

In the above embodiment, the prism 14 is in a form of a trapezoid as viewed in a section. However, the prism 14 can be in a form of a triangle as viewed in a section. Also, the prism 14 may be in a form of a semi-circle or any suitable closed loop as viewed in a section. In the above embodiment, the protecting panels 72 or the protection layer 102 is disposed on a surface of the prism 14. However, the protecting panels 72 or the protection layer 102 may be positioned to lie on any suitable point where light paths of entrance and exit are defined.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it possible to measure the interaction on the sensing surface.

Also, various materials may be used for protecting panels or elements disposed close to the prism according to the invention. Examples of various materials for such used are disclosed in U.S. Pat. No. 4,575,240 (corresponding to JP-B 6-003414) and the like.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A sensor unit comprising:
    a dielectric block provided with a thin film disposed on a surface thereof, wherein:
        said thin film comprises a sensing surface for detecting a reaction of a sample,
        illuminating light is applied to an interface in a form satisfying a total reflection condition, wherein said interface is disposed between said thin film and said dielectric block, and
        when said sample in a sample fluid contacts said sensing surface, a resonance angle for creating surface plasmon resonance is changed by said reaction of said sample, and
    a protection layer overlaid on an outer surface of said dielectric block, wherein said protection layer protects a first region of said dielectric block that passes said illuminating light that is incident on said interface, and a second region of said dielectric block that passes light reflected by said interface,
    wherein said dielectric block is constituted by a prism having a polygonal shape as viewed in a section, said surface with said thin film is directed upwards, and said protection layer is positioned on two outer surfaces of said prism, and
    wherein said protection layer is constituted by a peelable protection tape, and said protection tape is peeled away before assay of said reaction of said sample.

2. A sensor unit as defined in claim 1, wherein said protection layer is transparent and formed by applying a coating to said outer surface.

3. A sensor unit as defined in claim 2, wherein said protection layer is formed from a material containing at least one of fluoride and titanium oxide.

* * * * *